United States Patent [19]
Bolden et al.

[11] Patent Number: 5,721,676
[45] Date of Patent: Feb. 24, 1998

[54] CENTRIFUGE DATA COMMUNICATIONS SYSTEM

[75] Inventors: Paul Anthony Bolden, Woodbury; Thomas Raymond Poulin, Southbury, both of Conn.

[73] Assignee: Sorvall Products, L.P., Newtown, Conn.

[21] Appl. No.: 544,680

[22] Filed: Oct. 18, 1995

[51] Int. Cl.$^6$ ................................................. G06F 19/00
[52] U.S. Cl. ..................... 364/132; 364/497; 422/72; 436/45
[58] Field of Search ................... 364/138, 139, 364/131–136, 550, 551.01, 496–500, 188, 189; 422/72, 68.1, 62, 63–67, 44, 105–116, 119; 436/43, 45, 50, 55; 494/1, 7, 10, 11, 16, 37

[56] References Cited

U.S. PATENT DOCUMENTS

| | | | |
|---|---|---|---|
| 4,707,834 | 11/1987 | Frisch et al. | 371/20.1 |
| 4,903,191 | 2/1990 | Fries | 364/187 X |
| 5,063,494 | 11/1991 | Davidowski et al. | 395/800 |
| 5,207,634 | 5/1993 | Greenstein | 494/10 |
| 5,287,265 | 2/1994 | Hall et al. | 364/188 |
| 5,399,262 | 3/1995 | Hawkins et al. | 210/195.1 |
| 5,428,470 | 6/1995 | Labriola | 364/497 X |
| 5,449,621 | 9/1995 | Klein | 436/45 |
| 5,454,777 | 10/1995 | Ziems et al. | 494/8 |
| 5,492,831 | 2/1996 | Ranger | 436/50 |
| 5,568,262 | 10/1996 | LaChapelle et al. | 356/379 |

OTHER PUBLICATIONS

EIA–485, Standard for Electrical Characteristics of Generators and Receivers for use in Balanced Digital Multipoint Systems, Electronic Industries Assoc., Apr. 1983.

IEEE Standards Project, P1073, Standard for Medical Device Communications Overview and Framework, May 1992.

*Primary Examiner*—Joseph Ruggiero
*Attorney, Agent, or Firm*—Ohlandt, Greeley, Ruggiero & Perle

[57] ABSTRACT

A data communications system for a plurality of centrifuge instruments, each with a local controller, includes a central data controller and a communication link that connects the central data controller to each of the instrument controllers. The link complies with Electronic Industries Association (EIA) Standard 485. The central data controller transmits a predetermined command and an instrument address signal over the link. Each instrument controller is responsive to the transmission of the command signal and to its respective instrument address signal by transmitting to the central data controller over the communications link the then-current values of at least some of the set of operational parameters for the particular centrifuge instrument.

6 Claims, 6 Drawing Sheets

CENTRIFUGE DATA COMMUNICATIONS SYSTEM

BACKGROUND OF THE INVENTION

1. Field of Invention

The present invention relates to a data communications system for a plurality of centrifuge instruments.

2. Description of Prior Art

The input to the blood supply system in the United States is a network of blood bank centers which serve to collect, process and distribute human blood. Each center contains a plurality of blood processing centrifuge instruments, such as the instruments manufactured by the Centrifuge Products Division of E. I. du Pont de Nemours and Company and sold as the RC-3 family of instruments. A relatively large blood bank center has on the order of sixteen centrifuge instruments.

The centers are subject to regulation to maintain tight control over both the inventory of and quality of this blood supply. To achieve this level of control most blood banks use a bar coding system wherein a bar code label is affixed to the bag of donated blood at the time of donation. The blood bank can thereafter track the path of the blood bag as it works through the system while maintaining the confidentiality of the donor.

Food and Drug Administration's regulations [particularly, Standard for Good Manufacturing Practices (GMP)—Blood and Blood Components, Part 606.60 subpart D—Equipment] mandate that before blood bank production can begin each day a set of quality control ("QC") protocols must be performed on each centrifuge instrument. The purpose of the QC protocols is to insure that each centrifuge instrument is able to perform properly each protocol that is anticipated being executed by that instrument during the upcoming production day. On a typical production day each instrument in the blood bank would be called upon to perform five or six different protocols.

To perform the QC protocols an operator must set the instrument for the appropriate speed and temperature of the protocol, start the instrument and permit it to run for several minutes before recording the final actual speed and temperature. This procedure must be repeated for each protocol. After the set of QC protocols is completed the results must be approved by a supervisor before a given centrifuge instrument can be operated in production. The daily production at a center may be delayed until the QC protocols are approved.

It is anticipated that in addition to the daily QC requirements future regulations may require documentation regarding every production run processed by each instrument during a production day. Such a documentation requirement will help insure that not only are the instruments running properly throughout the production day, but that the operators have used the appropriate protocol for each production run.

The presently mandated daily QC protocols and the anticipated documentation requirements for regular production runs are seen as being extremely labor intensive. Accordingly, in view of the foregoing, it is considered advantageous to provide a system that automates the performance of the presently mandated QC protocols and that would also permit automatic documentation of regular production runs.

SUMMARY OF INVENTION

The present invention is directed toward a data communications system for a plurality of centrifuge instruments. Each instrument has a programmable instrument controller therein. The programmable instrument controller is adapted to control the operation of the centrifuge instrument with which it is associated in accordance with a predetermined set of operational parameters. The set of operational parameters includes, for example, maximum rotational speed, temperature, time of centrifugation, acceleration to operational speed, deceleration from operational speed, relative centrifugal force (RCF) and the parameter $\omega^2 dt$.

The data communications system is comprised of a central data controller and a communication link connecting the central data controller to each of the instrument controllers. The central data controller has a memory therein. The communications link connects the central data controller to each of the instrument controllers in accordance with Electronic Industries Association (EIA) Standard 485.

The central data controller is operative to transmit a predetermined command signal and a predetermined instrument address signal over the link. Each instrument controller is responsive to the transmission of the command signal and to its respective instrument address signal by transmitting to the central data controller over the communications link the then-current values of at least some of the set of operational parameters for the particular centrifuge instrument.

Each centrifuge instrument has a bar code reader associated therewith. The values read by the bar code reader are stored by the instrument controller in a suitable memory provided in the instrument controller. In response to a command signal and its respective instrument address signal the instrument controller transmits the values of the bar codes read by the bar code reader and stored by the instrument controller to the central data controller.

BRIEF DESCRIPTION OF DRAWINGS

The invention will be more fully understood from the following detailed description, taken in connection with the accompanying drawings, in which.

DETAILED DESCRIPTION OF THE INVENTION

Throughout the following detailed description similar reference characters refer to similar elements in all Figures of the drawings.

Figure 1:
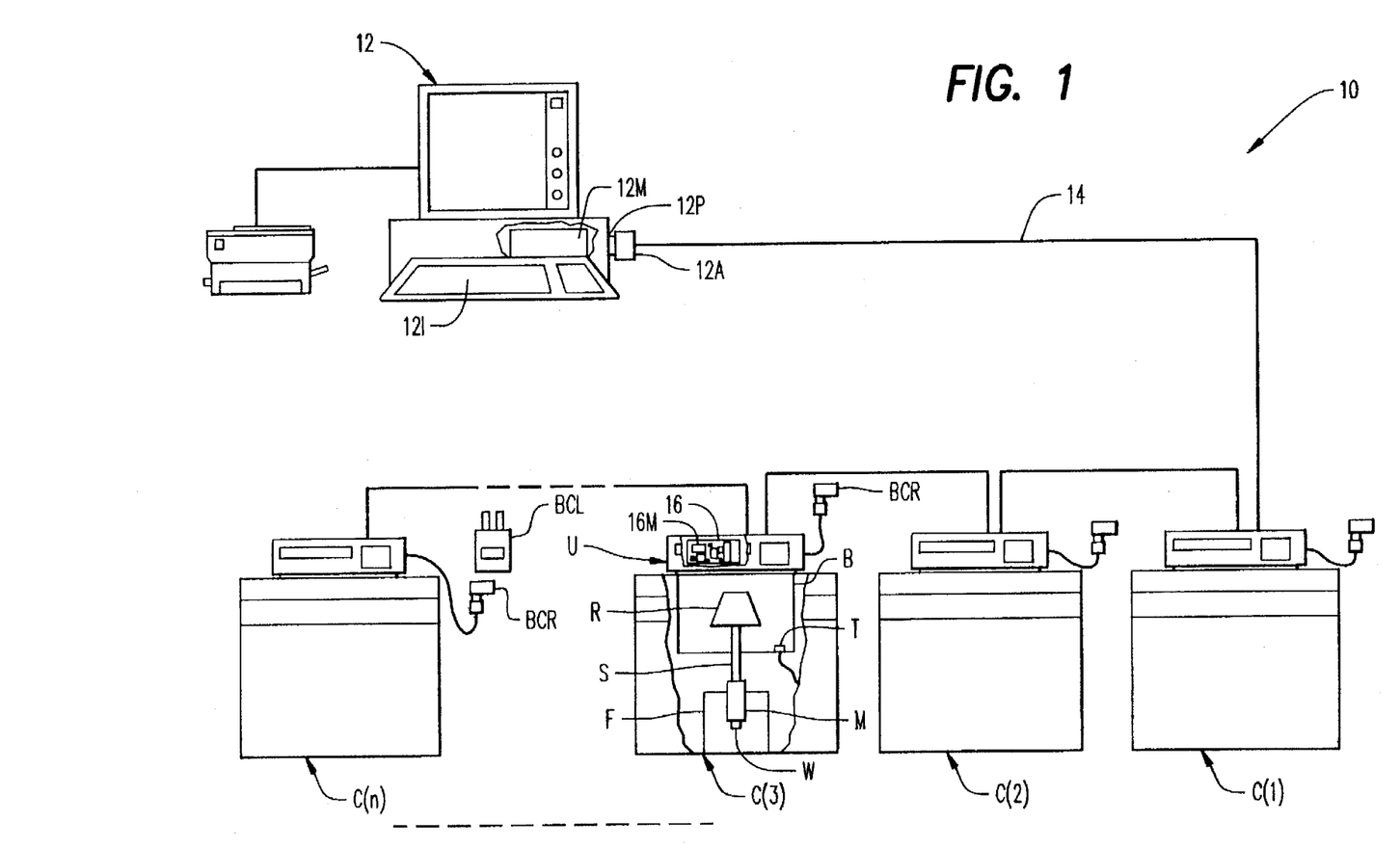
FIG. 1 is a block diagrammatic representation of a typical blood center within which a communications system of the present invention may be used.

FIG. 1 illustrates a data communications system generally indicated by the reference character 10 in accordance with the present invention as implemented in the environment of a relatively large blood bank center. As will be developed the data communications system 10 includes a central data controller 12 and a communications link 14. The communications link 14 complies with the Electronic Industries Association Standard for Electrical Characteristics of Generators and Receivers for Use in Balanced Digital Multipoint Systems, EIA-485 (April 1983). This standard is hereby incorporated by reference.

A relatively large blood bank center will contain a number n of blood processing centrifuges denoted in FIG. 1 by the reference character C(1) through C(n). For any given blood bank center the number n represents any convenient number of centrifuge instruments. Typically the number n is on the order of sixteen instruments. The centrifuge instruments C(1) through C(n) in FIG. 1 are shown as being linked to each other and to the central data controller 12 via the communications link 14.

Each blood processing centrifuge C(1) through C(n) has a framework F within which a motor M is suspended. The motor M provides motive force to a shaft S that extends centrally and axially through the framework F. The shaft S is adapted to accept a blood processing rotor R. The rotor R has a plurality of receptacles therein, each receptacle being adapted to receive a blood bag. Attached to the shaft S, usually on the opposing end, is a tachometer device W that monitors the rotational speed of the shaft S.

Within the framework F of each centrifuge instrument there is an open-topped chamber, or bowl B, with a centrally located opening through which the shaft S of the motor extends. Surrounding the bowl B are refrigeration tubes that carry a gaseous refrigerant in a closed refrigeration loop including a condenser unit and a compressor unit. Both the condenser and compressor units are housed within the framework of the centrifuge instrument. Attached to and extending into the bowl B is a thermoelectric transducer T which usually takes the form of either a thermocouple or a thermal sensing chip such as the Analog Devices AD590. The thermoelectric transducer T monitors the air temperature of the bowl B.

A user control panel U is located on each instrument which allows a clinician to set the various operational parameters required for a centrifugation run. Typically the set of operational parameters includes maximum rotational speed of the rotor R, temperature within the bowl B, time of centrifugation, acceleration to operational speed, deceleration from operational speed, relative centrifugal force (RCF), and the parameter $\omega^2 dt$. Additionally the user control panel U includes the instrument "Start" and "Stop" buttons.

Each centrifuge instrument C includes a local instrument controller 16 which controls the operation of the centrifuge instrument. The instrument controller 16 is typically implemented using a microprocessor-based computer system operating under the control of a program. The instrument controller 16 includes a suitable memory 16M therein. The local instrument controller 16 controls the operation of the centrifuge instrument with which it is associated in accordance with the user-selected operational parameters input via the control panel U. To this end the various signal outputs from the various transducers disposed within the instrument, such as the outputs from the thermoelectric transducer T and the tachometer device W, are applied to, stored by, and used by the local controller 16 to control instrument operation.

Each instrument C also has a bar code reader BCR associated therewith. The bar code reader BCR is operative to read the bar code label BCL affixed to each bag of blood processed by each instrument. The bar code reader BCR is connected to the local instrument controller 16 so that bar code information may be stored in the memory 16M thereof.

The heart of the data communications system 10 in accordance with the present invention is the central data controller generally indicated by the reference character 12. The central data controller 12 is preferably implemented using an IBM-compatible personal computer, such as a Dell Optiplex 466/LV, having a 486-class CPU running at a clock speed of sixty-six MHz with at least eight MB of random access memory. The central data controller 12 is equipped with RS232 serial communications circuitry including a port 12P and an adapter 12A allowing the port 12P to connect with the communications link 14 operating under Electronic Industries Association (EIA) Standard 485. The central data controller 12 is hereafter sometimes referred to as "central" 12. Central 12 is connected to each centrifuge instrument C(1) through C(n) over the communications link 14. Each centrifuge instrument C(1) through C(n) connected to the data communications network 10 over the communications link 14 has a predetermined address associated therewith.

Central 12 has a magnetic storage device 12M (e.g., a hard drive) that allows long term storage of both its executing software as well as the data collected in a manner to be described over the communications link 14 from the centrifuge instruments C(1) through C(n). The central data controller 12 includes a suitable user interface 12I whereby commands and information may be exchanged between the user and the controller 12, thereby to allow a clinician to input into memory various commands and data for use in the controlling software. Central 12 also has a display in the form of a monitor (e.g., a CRT) for visual presentation of the results collected by the controlling software.

Central 12, under the control of its program, is operative to accept input from a clinician (through the user interface 12I) and issue desired command(s) and respective address signals to the data communications link 14. As will discussed in more detail herein the command and address are received by the local instrument controller 16 in each of the centrifuge instruments. The instrument controller 16 compares the address portion of the signal with the address of the centrifuge instrument and if a match occurs, the command is executed. Information is sent from the local instrument controller 16 via the communications link 14 to central 12.

In use, the communications system of the present invention serves to automate several tasks in the blood supply system that are seen as labor intensive, such as the performance of QC protocols or the logging of daily production runs. The manner in which the data communications system 10 may be used to perform QC protocols for each instrument C(1) through C(n) or to log production information from an instrument C(1) through C(n) may be understood from the following discussion, taken in connection with FIGS. 2A, 2B and 3A through 3C.

Figure 2A:
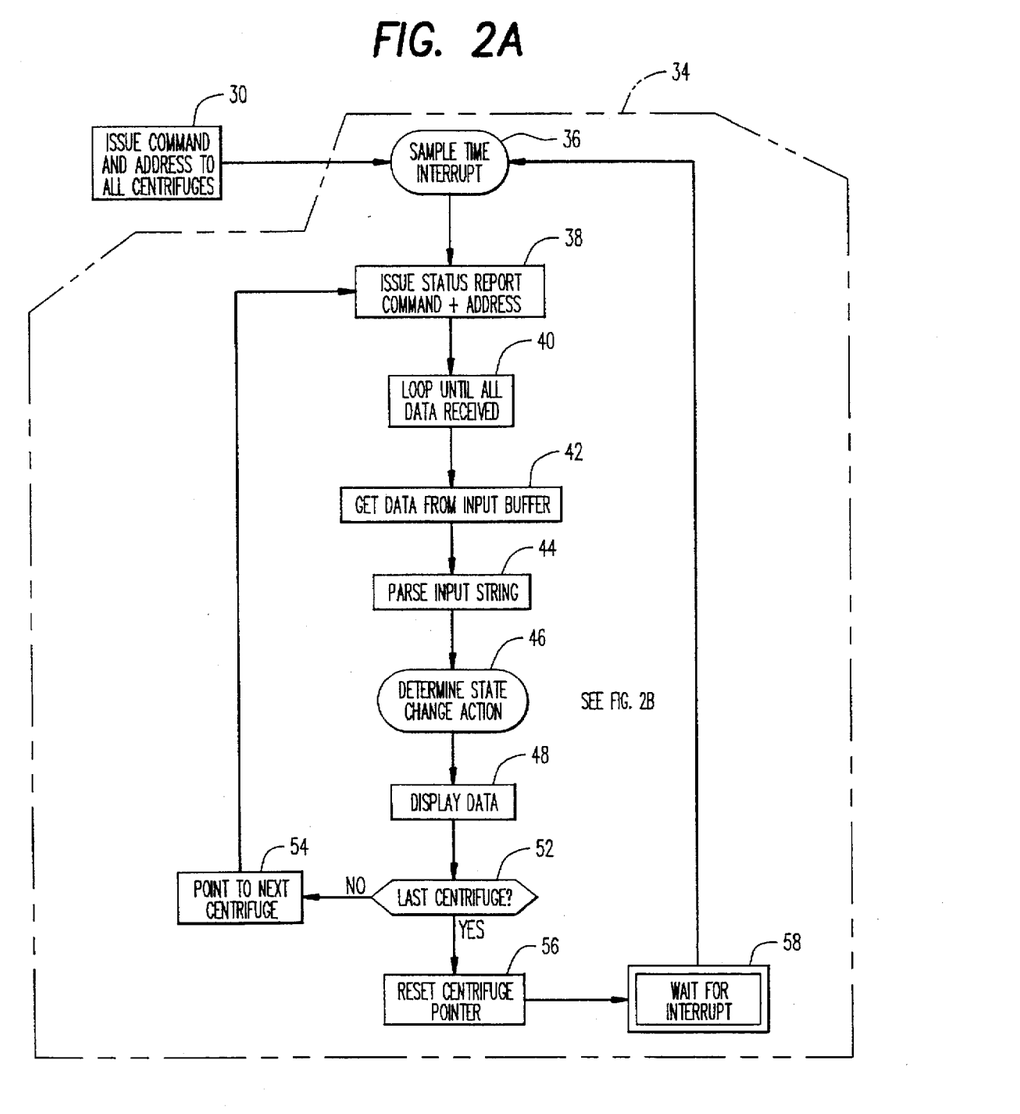
FIGS. 2A and 2B are high level flow diagrams of a program for the central data controller for implementing the communications system of the present invention.
Figure 2B:
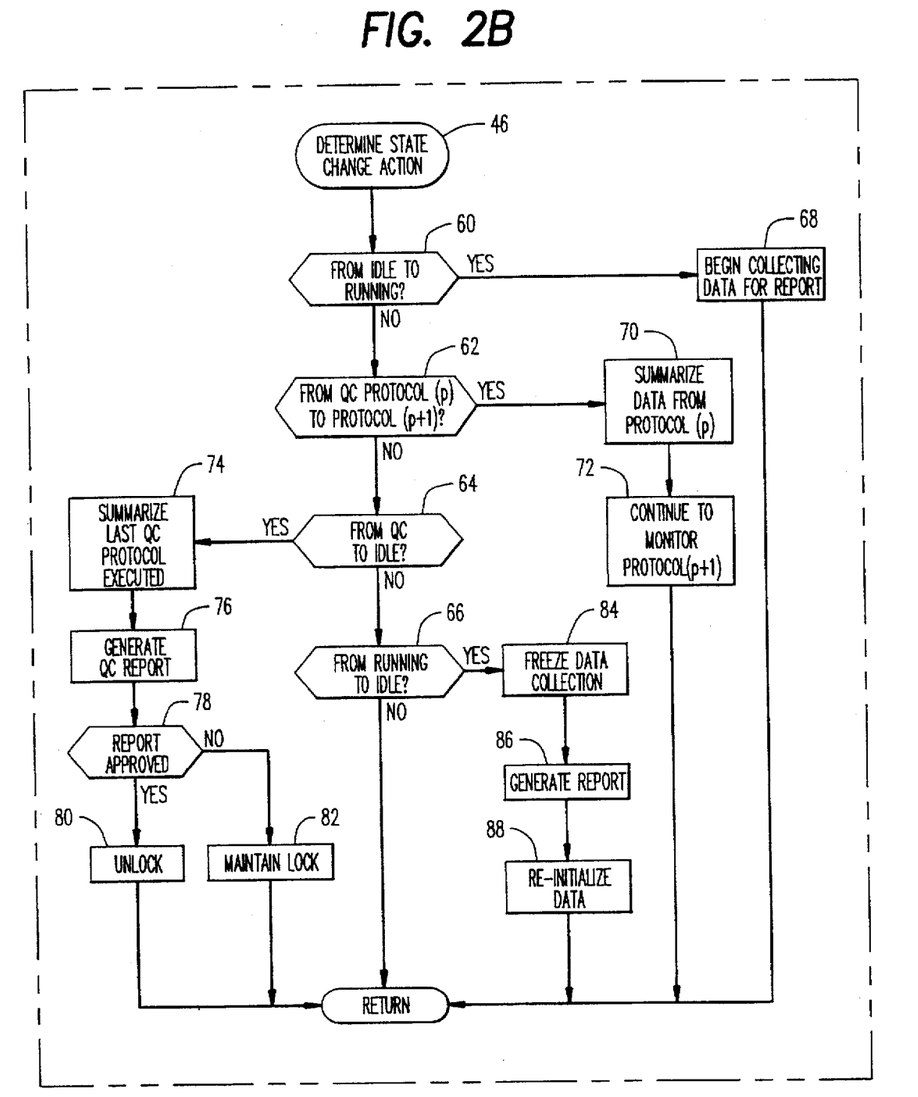

The flow diagram of the actions of central 12 are shown in FIGS. 2A and 2B. The flow diagram of FIG. 2A is discussed first. As the result of either an overt action by a clinician or in automatic response to its program the central data controller 12 issues a message over the link 14. The message comprises a predetermined command and an address. This action is indicated in block 30 (FIG. 2A). The issued command may, for example, be either a QC command or a "status report" command. The command is issued together with a respective address signal for each centrifuge instrument C(1) through C(n). The command may be addressed to each instrument individually (in any predetermined sequence) or the command may be issued with an "all instruments" address. In either case the addressed local controller 16, upon receipt of the command, begins to execute the requested activity. The activity of the local controller 16 proceeds asynchronously with respect to the actions of the central data controller 12. Details of the action of each local controller 16 are described in connection with FIGS. 3A through 3C.

Since the local controller 16 acts asynchronously, following the transmission of the command and addresses, central 12 periodically polls the local processors in anticipation of a response. The activities of the central data controller 12 during the polling is indicated generally by the block 34 in FIG. 2A. The central 12 initiates polling of the instruments C(1) through C(n) upon the generation of an interrupt 36. As indicated generally by the block 38 the central 12 issues a "status report" command with the appropriate address to the first instrument being polled [typically, the instrument C(1)]. The status report command instructs the particular centrifuge instrument to report its operational parameters, such as current speed and set speed, chamber temperature and time, to central 12. It is again noted that the activities of the local controller 16 in response to this command will be discussed in connection with FIGS. 3A through 3C.

Central 12 idles until the response from the first addressed instrument is received, as indicated by the block 40. Data received from the responsive transmission from the first polled instrument is accessed from the central's input buffer (block 42). The data string is parsed (block 44) and a determination is made by central 12 whether any change of state of the instrument has occurred from the previous polling (if any). The determination of change of state is indicated in FIG. 2A by the block 46 and is shown in more detail in FIG. 2B. Any necessary display of data from the first polled instrument is made (block 48). Central 12 proceeds to poll the other remaining instruments, as indicated by the actions of the decision block 52 and the address pointer 54. Upon receipt of the data from the last of the polled instruments the instrument pointer is reset to the first instrument (block 56). Central 12 idles until the next occurrence of the interrupt 36. Upon receipt of the interrupt (block 58) the poll of all of the instruments C(1) through C(n) is repeated. The duration of the interval during which the central 12 polls of the entire set of instruments C(1) through C(n) (i.e., block 34) requires on the order of two seconds.

Figure 3A:
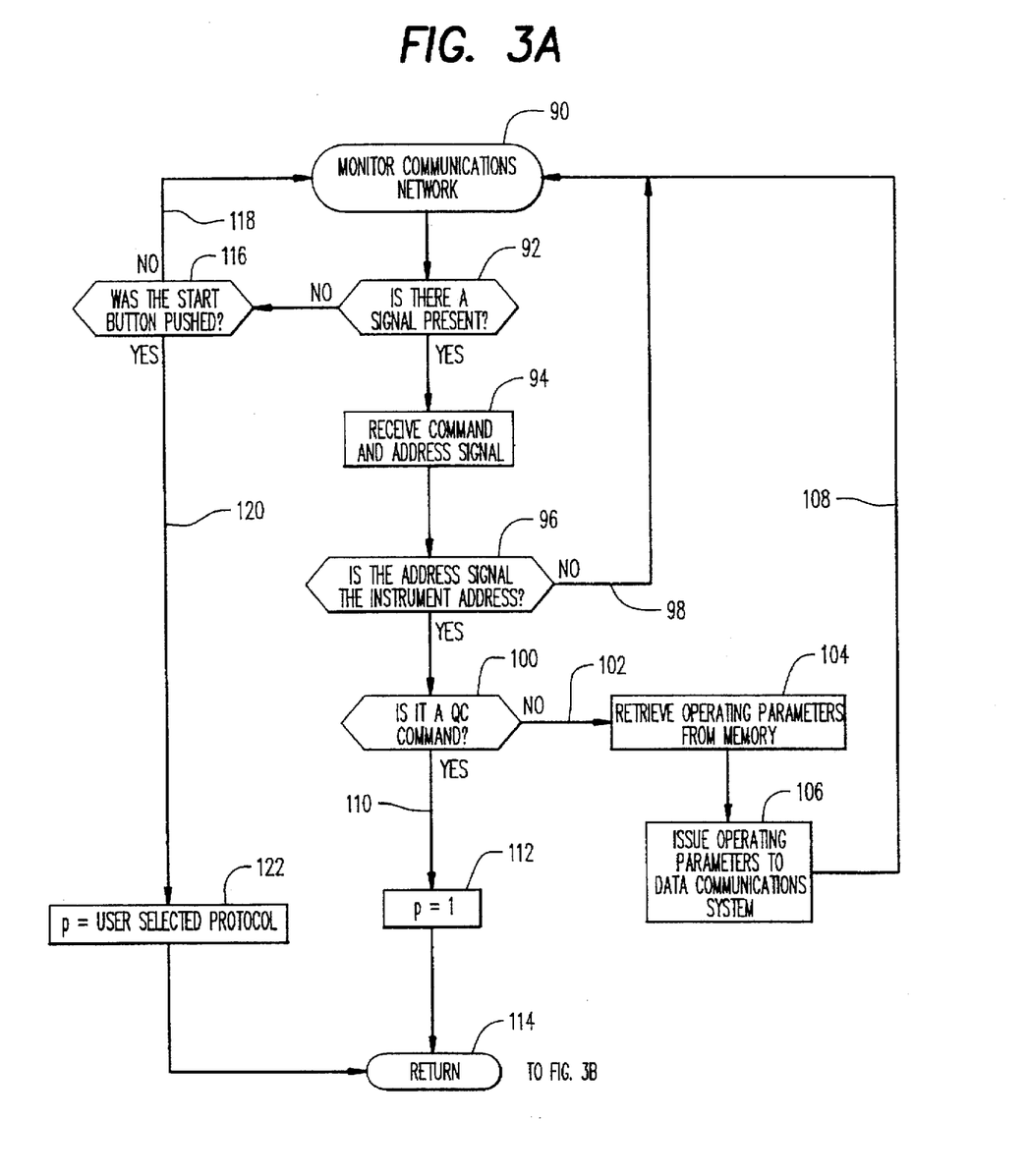
FIGS. 3A through 3C are high level flow diagrams of a program for the use by the instrument controllers in responding to command and address signals output by the central data controller in accordance with the communication system of the present invention.
Figure 3B:
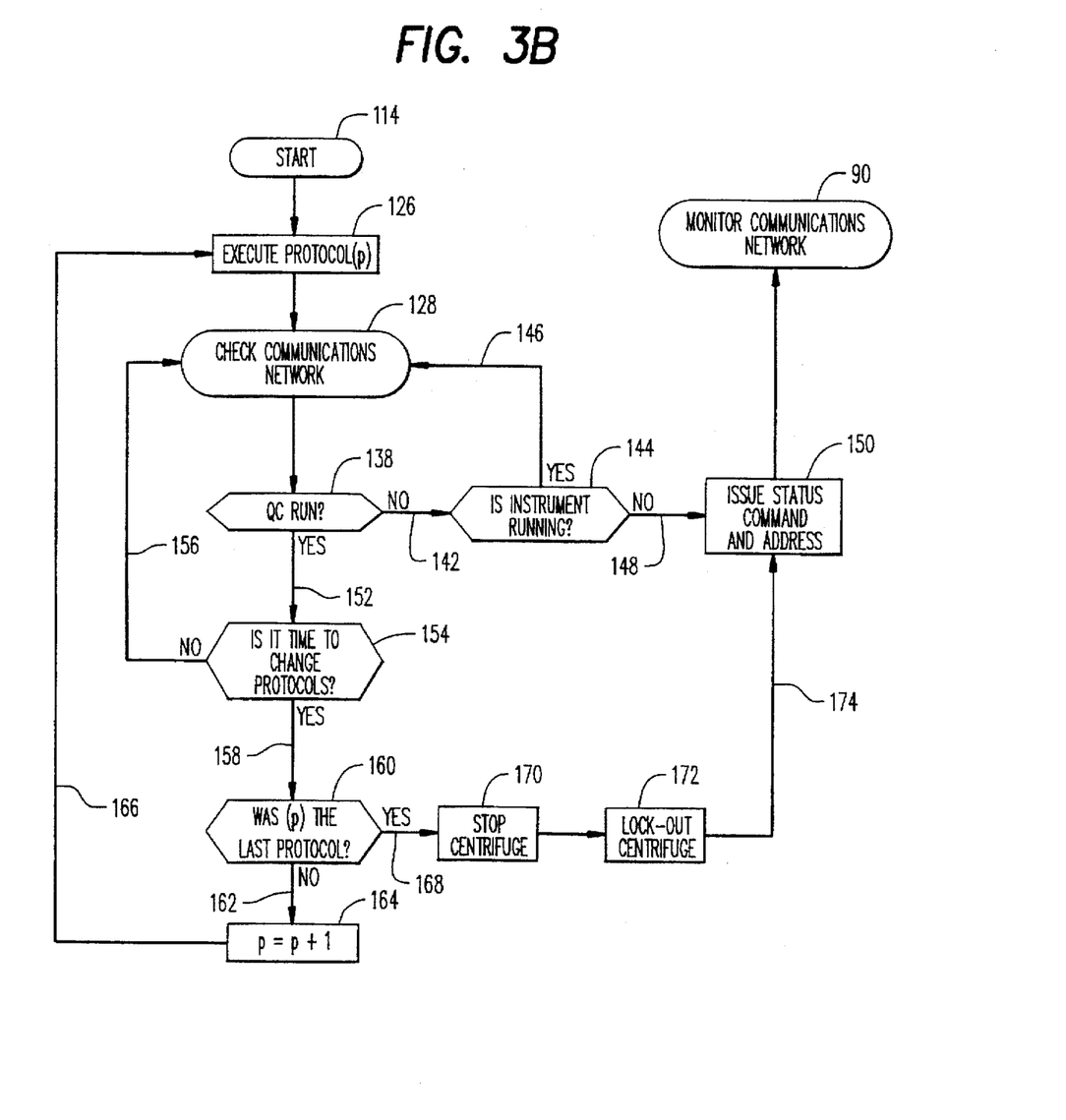
Figure 3C:
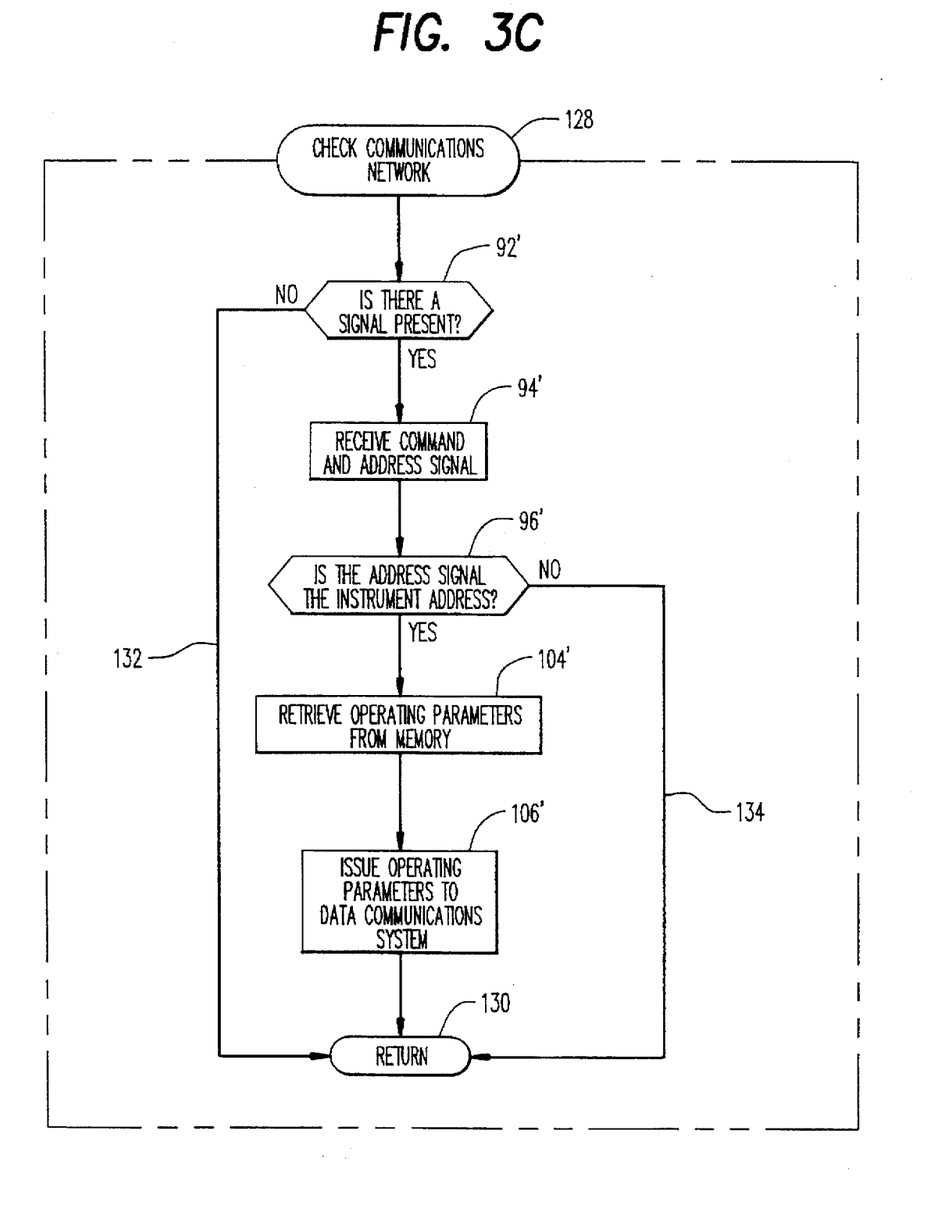

The activities of each local controller 16 for the instruments C(1) through C(n) in the context of the present invention may be understood with reference to FIGS. 3A through 3C. Each local controller 16 monitors the link 14 as indicated by the block 90 (FIG. 3A) for the receipt of the initial message (command and address) output from central 12 (block 30, FIG. 2A). If a determination is made that a message is present on the link 14 (block 92) the signals are received into the input buffer of the local controller 16 (block 94). The address portion of the received message is examined to determine if it corresponds to the address assigned to the particular local controller 16 under consideration, as shown in the decision block 96. If the addresses do not match the local controller 16 reverts to the link monitoring state 90 (via branch 98). However, if the received address corresponds to the address of the local controller 16, the local controller 16 examines the command portion of the message to determine if a QC or a status report command has been issued (block 100). If a status report command has been issued (branch 102) the local controller 16 retrieves at least some or all of the current values of the set of instrument operating parameters stored in its memory (block 104) and transmits the same to central 12 over the link 14 (block 106). The local controller 16 then reverts to the link monitoring state 90 (via branch 108). If the received command is a QC command (branch 110) a protocol identity pointer (block 112) is set to the first of the "P" number of protocols that must be performed to satisfy a quality control check of the instrument. The local controller 16 then branches (block 114) to begin the execution of the QC routine (FIG. 3B).

If no signal is present on the link 14, as determined by the decision block 92, the local controller 16 determines whether the instrument "Start" button has been asserted, as at block 116. If not, the local controller 16 reverts to the link monitoring state 90 (via branch 118). If the instrument "Start" button has been asserted the protocol identity pointer is set to correspond to the identity of the protocol selected by the user (block 122), and the local controller 16 then branches (block 114) to begin the execution of the selected protocol (FIG. 3B).

With reference to FIG. 3B, as indicated by the block 126, the local controller 16 begins to execute the protocol as directed by the protocol identity pointer (blocks 112, 122). In the block 128 the local controller 16 checks the communications link 14 for the presence of the "status report" command (block 38, FIG. 2A). The steps involved in the check of the communications link 14 are set forth in FIG. 3C. This activity of the local controller 16 is basically similar to the portion of the routine indicated in FIG. 3A by the blocks 92, 94, 96, 104 and 106. Accordingly, blocks of the "check communications" routine 128 that correspond to activities discussed in FIG. 3A are indicated by primed reference numbers. If a message is present of the link 14 (block 92') the signals are received into the input buffer of the local controller 16 (block 94'). If the address portion of the received message corresponds to the address of the local controller 16 (block 96') the local controller 16 retrieves the then-current values of the set of instrument operating parameters present in its memory (block 104') and transmits at least some or all of the then-current values of the set of instrument operating parameters to central 12 over the link 14 (block 106'). The local controller 16 then returns (block 130) to continue the routine of FIG. 3B. If no message is present on the link (block 92') or if the addresses do not match (block 96'), the local controller 16 returns (block 130) to the routine of FIG. 3B, via branches 132 and 134, respectively.

Reverting to FIG. 3B, after transmitting at least some or all of the then-current values of its operating parameters (block 104') further action of the local controller 16 is determined by whether it is responding to a QC command or to a "status report" command from the central 12 (block 138). If a QC command has not been issued (branch 142) and the instrument is still operating (block 144) the local controller 16 continues to loop through and report in accordance with the routine 128 (FIG. 3C). If the instrument is not running (i.e., the requested protocol is finished) the local controller 16, via the branch 148, issues a status report to central 12 over the link 14 (block 150) and reverts to the monitoring of the communications link (block 90, FIG. 3A).

However, if a QC command has been issued (branch 152) and the instrument has not yet finished running the then-current protocol for QC purposes (block 154) the local controller 16 (via branch 156) loops through and reports in accordance with the routine 128 (FIG. 3C). If the instrument has finished the then-current protocol (via branch 158), the local controller 16 determines whether additional protocols remain to be performed to complete the QC routine (block 160). If additional protocol(s) are to be performed (branch 162) the protocol identity pointer is incremented (block 164). The local controller 16, via the branch 166, changes the operating parameters to correspond to the next preprogrammed protocol, whereupon the instrument increases or decreases its speed and temperature to match the parameters in the pre-programmed protocol (block 126). Each additional protocol necessary to complete the QC routine is thus executed.

When the local controller 16 determines (block 160) that the last of the protocols has been executed (branch 168) the instrument is stopped (block 170) The local controller 16 "locks out" the instrument (block 172), thus disabling the instrument and preventing it from being used. Via the branch 174, the local controller 16 issues a status report to central 12 over the link 14 (block 150) and reverts to the monitoring of the communications link (block 90, FIG. 3A).

As has been developed each local controller 16 responds to the polling by central 12 (block 38, FIG. 2A) in accordance with the actions of block 106 (FIG. 3A), block 150 (FIG. 3B), or block 106' (FIG. 3C). Upon receipt of a transmission from a local controller 16, central 12 receives (block 42) and parses the data (block 44) The detailed description of the manner in which central 12 determines if any significant change of state has occurred (block 46) is shown in detail in FIG. 2B.

Upon receipt and parsing of the transmission from the local controller 16 (blocks 42, 44) central 12 compares the most current status information with respect to the information provided in the immediately preceding status report to make the following determinations: (1) whether a given instrument has passed from an idle to a running state (block 60); (2) whether a given instrument has incremented to the next succeeding protocol in connection with a QC routine (block 62); (3) whether a given instrument has passed from a QC routine to an idle state (block 64); or, (4) whether a given instrument has passed from a running to an idle to state (block 66).

The action of central 12 if an affirmative response from any of these decisions is illustrated in FIG. 2B. If given instrument has passed from an idle to a running state (block 60), central 12 begins data collection in anticipation of the issuance of a report (block 68). If given instrument increments to the next succeeding protocol in connection with a QC routine (block 62) central 12 summarizes and stores data from the preceding protocol (block 70) and continues to monitor the activity during the succeeding protocol (block 72) in accordance with the operations earlier set forth.

When a given instrument has passed from a QC routine to an idle state (block 64) central 12 summarizes from the information received from the last protocol (block 74) and, using data stored from previous protocols (block 70) generates a QC report (block 76). It will be recalled that upon completion of the last protocol the local controller 16 of a given instrument would lock-out the instrument (block 172, FIG. 3B). The maintenance of the lock-out condition is dependent upon the approval of the QC report. If the report is approved by the clinician via an input from the I/O interface 12I to the central controller 12 (block 78) the instrument is unlocked (block 80) by an "unlock" command issued from central 12 to the local controller 16. However, if the QC report is not approved the lock-out of the instrument is maintained (block 82). Finally, when a given instrument has passed from a running to an idle to state (block 66) central 12 freezes the collection of data (block 84), generates a report (block 86) and re-initializes its memory 12M (block 88).

In summary, in response to a QC command, the central controller 12, which monitors the operation of the QC run on a predetermined (e.g., two second) interrupt interval, collects data for each centrifuge instrument connected to the link 14. At the transition of each protocol central 12 summarizes the run and continues monitoring the next program. When central 12 receives a zero speed operating parameter from a particular centrifuge instrument central 12 generates a QC report summarizing the operating parameters monitored for each of the protocols. This QC report is reviewed by the clinician and if there are no problems with the performance of the particular centrifuge the report is approved. Approval of the QC report causes central 12 to issue an "unlock" command through the communications system to the particular centrifuge instrument. The "unlock" command then allows the instrument to be used in production.

Having described the operation of the present invention in the context of an issued QC command the response of the present invention to a "status report" command to log instrument performance in a production run should be readily understood. The documentation generated may be used show regulatory agencies what protocols are being performed, that they are being performed with the correct parameters, and that the instruments are operating within their specifications. First, the clinician loads a centrifuge instrument with the blood bags to be processed. As the instrument is loaded the bar code reader BCR scans the label BCL on each bag. The information read by the reader BCR is stored in the memory 16M of the local controller 16. A pre-programmed protocol is selected and the "Start" button is asserted (blocks 116, 122; FIG. 3A). Central 12, upon the determination of a change in state (block 46, FIG. 2A), such as a change from "idle" to "running" (block 60, FIG. 2B), may send a "bag data" command and address. The local controller 16 in response to this command signal and respective instrument address, transmits to central 12 the values of the bar codes stored within the memory 16M of the instrument controller 16. Central 12, at predetermined interval intervals (block 36) sends a "status report" command and a respective address signal through the communications network (block 38) to the local controller 16 of a centrifuge instrument requesting information such as time remaining, current speed, current temperature, set time, set speed, set temperature and protocol number. Upon receiving this request the local controller 16 responds over the communications link 14 (blocks 106', 150) with the appropriate information. Central 12 receives the information (block 42) and appropriately displays (block 48) or otherwise stores it for further use.

Those skilled in the art, having the benefit of the teachings of the present invention may impart numerous modifications thereto. Such modifications are to be construed as lying within the contemplation of the scope of the present invention, as defined by the appended claims.

What is claimed is:

1. A data communications system for a plurality of centrifuge instruments, each instrument having a programmable instrument controller therein, each said programmable instrument controller being adapted to control the operation of the centrifuge instrument with which it is associated in accordance with a predetermined set of operational parameters, wherein said data communications system comprises:

a central data controller having memory therein, and a communication link connecting said central data controller to each of the programmable instrument controllers for communication therebetween, said central data controller being operative to transmit a predetermined command signal and a predetermined instrument address signal over said communication link, each said programmable instrument controller being responsive to the transmission of said predetermined command signal and to its respective instrument address signal by transmitting to said central data controller over said communications link the then-current values of at least some of the set of operational parameters for the particular centrifuge instrument.

2. The data communications system of claim 1 wherein each centrifuge instrument has a bar code reader associated therewith, and wherein each instrument controller has a memory disposed therein, values read by the bar code reader being stored in the memory of the instrument controller, the instrument controller, in response to a command signal and to its respective instrument address signal, being operative to transmit to the central data controller the values of the bar codes read by the bar code reader and stored within the instrument controller.

3. The data communications system of claim 1, wherein when the then-current values transmitted by a single programmable instrument controller signify completion of a task by the particular centrifuge instrument it controls, said single programmable instrument controller disables the particular centrifuge instrument until said central data controller issues an unlock command to said single programmable instrument controller.

4. The data communications system of claim 3, wherein said central data controller issues an unlock command to said single programmable instrument controller when data characterizing said task are approved.

5. The data communications system of claim 4, wherein said data characterizing said task are approved by a clinician via an input to an I/O interface to said central data controller.

6. The data communications system of claim 3, wherein said task is a QC protocol.

* * * * *